United States Patent
Davis

(10) Patent No.: US 11,083,765 B2
(45) Date of Patent: Aug. 10, 2021

(54) HEMP LEAF CHEW COMPOSITION AND METHOD FOR PRODUCING

(71) Applicant: Andrew Scott Davis, Santa Barbara, CA (US)

(72) Inventor: Andrew Scott Davis, Santa Barbara, CA (US)

(73) Assignee: Andrew Scott Davis, Santa Barbara, CA (US)

(*) Notice: Subject to any disclaimer, the term of this patent is extended or adjusted under 35 U.S.C. 154(b) by 51 days.

(21) Appl. No.: 15/844,217

(22) Filed: Dec. 15, 2017

(65) Prior Publication Data

US 2019/0183951 A1  Jun. 20, 2019

(51) Int. Cl.
| | | |
|---|---|---|
| *A61K 36/185* | (2006.01) | |
| *A61K 31/352* | (2006.01) | |
| *A24B 15/40* | (2006.01) | |
| *A61K 9/00* | (2006.01) | |
| *A24B 15/16* | (2020.01) | |
| *A61K 31/05* | (2006.01) | |
| *A24B 13/00* | (2006.01) | |

(52) U.S. Cl.
CPC ............ *A61K 36/185* (2013.01); *A24B 13/00* (2013.01); *A24B 15/16* (2013.01); *A24B 15/403* (2013.01); *A61K 9/006* (2013.01); *A61K 9/0056* (2013.01); *A61K 31/05* (2013.01); *A61K 31/352* (2013.01)

(58) Field of Classification Search
CPC .... A61K 36/185; A61K 31/352; A61K 9/006; A26B 15/16; A24B 15/403
See application file for complete search history.

(56) References Cited

U.S. PATENT DOCUMENTS

| | | | | |
|---|---|---|---|---|
| 5,612,074 A | * | 3/1997 | Leach | ..................... A23L 7/126 426/102 |
| 6,563,009 B1 | * | 5/2003 | Kunos | ..................... A61K 31/05 568/743 |
| 8,906,429 B1 | * | 12/2014 | Kolsky | ................ A61K 36/185 424/725 |
| 9,044,390 B1 | * | 6/2015 | Speier | ..................... A61K 36/00 |
| 9,066,910 B2 | * | 6/2015 | Rosenblatt | ........... A61K 36/185 |
| 9,415,082 B1 | * | 8/2016 | Davis | ..................... A61K 36/53 |
| 9,901,607 B2 | | 2/2018 | Silen | |
| 2004/0049059 A1 | * | 3/2004 | Mueller | ................. A61K 31/35 549/390 |
| 2004/0147767 A1 | * | 7/2004 | Whittle | .............. B01D 11/0242 549/390 |

(Continued)

FOREIGN PATENT DOCUMENTS

| | | | |
|---|---|---|---|
| BE | 584191 | * | 10/1959 |
| BE | 584191 | * | 5/1960 |

OTHER PUBLICATIONS

Safety and Toxicology of Cannabinoids (Year: 2015).*

(Continued)

*Primary Examiner* — Francisco W Tschen
*Assistant Examiner* — Guy F Mongelli
(74) *Attorney, Agent, or Firm* — Steptoe & Johnson LLP

(57) ABSTRACT

A method for preparing a hemp leaf chew includes decarboxylating hemp and then mixing decarboxylated hemp with a syrup to create the hemp leaf chew. The hemp leaf chew is meant to be chewed by a user similar to chewing tobacco. The method may further include dosing the hemp leaf chew with THC.

9 Claims, 1 Drawing Sheet

(56) References Cited

U.S. PATENT DOCUMENTS

| | | | | |
|---|---|---|---|---|
| 2005/0080168 | A1* | 4/2005 | Medoff | B29B 17/0026 524/13 |
| 2006/0051489 | A1* | 3/2006 | Higgs | A23J 1/14 426/630 |
| 2007/0085059 | A1* | 4/2007 | Mora-Gutierrez | A61K 31/6615 252/400.21 |
| 2007/0248635 | A1* | 10/2007 | Jensen | A44C 15/002 424/402 |
| 2008/0317891 | A1* | 12/2008 | Anderson | A61K 36/185 424/776 |
| 2009/0092657 | A1* | 4/2009 | Burke | A61K 9/0095 424/439 |
| 2010/0126520 | A1* | 5/2010 | Clayton | A24B 13/00 131/277 |
| 2010/0226904 | A1* | 9/2010 | Davis | A61K 9/0056 424/94.1 |
| 2011/0129517 | A1* | 6/2011 | Rudolph | A61K 47/26 424/440 |
| 2012/0032369 | A1* | 2/2012 | Diamond | B01J 20/24 264/140 |
| 2012/0046351 | A1* | 2/2012 | Hospodor | A23G 1/42 514/454 |
| 2012/0046352 | A1* | 2/2012 | Hospodor | A23G 1/48 514/454 |
| 2012/0295968 | A1* | 11/2012 | Kelly | A61K 31/194 514/454 |
| 2013/0280320 | A1* | 10/2013 | Mompon | A61Q 19/00 424/443 |
| 2013/0295172 | A1* | 11/2013 | Freeman | A61K 31/352 424/456 |
| 2103/0295172 | * | 11/2013 | Freeman | A61K 36/185 800/260 |
| 2013/0337052 | A1* | 12/2013 | Linert | A61K 31/164 424/451 |
| 2014/0017177 | A1* | 1/2014 | Jones | A61K 31/444 424/48 |
| 2014/0038485 | A1* | 2/2014 | Anderson | D04H 1/587 442/180 |
| 2014/0166028 | A1* | 6/2014 | Fuisz | A24D 1/002 131/328 |
| 2014/0287068 | A1* | 9/2014 | Lewis | A01H 1/04 424/725 |
| 2014/0298511 | A1* | 10/2014 | Lewis | A01H 5/02 800/260 |
| 2015/0038567 | A1* | 2/2015 | Herkenroth | C07D 311/80 514/454 |
| 2015/0096574 | A1* | 4/2015 | Gao | A24B 15/16 131/275 |
| 2015/0181838 | A1* | 7/2015 | Epema | A01K 5/01 119/52.1 |
| 2015/0181839 | A1* | 7/2015 | Baikie | A01K 15/026 119/710 |
| 2016/0058696 | A1* | 3/2016 | Kim | A61Q 19/007 424/520 |
| 2016/0158299 | A1* | 6/2016 | Bohus | A61K 31/05 424/725 |
| 2016/0295860 | A1* | 10/2016 | Dagher | A23L 3/3508 |
| 2016/0296464 | A1* | 10/2016 | Lindsay | A61K 9/009 |
| 2016/0324908 | A1* | 11/2016 | Bates | A61K 36/185 |
| 2016/0325288 | A1* | 11/2016 | Bates | B02C 23/10 |
| 2016/0354310 | A1* | 12/2016 | Bachmann | A23G 4/12 |
| 2017/0022132 | A1* | 1/2017 | Mona, III | B01D 3/106 |
| 2017/0165224 | A1* | 6/2017 | Kwiecinski | A61K 9/009 |
| 2017/0215472 | A1* | 8/2017 | Dube | C13K 1/04 |
| 2017/0274027 | A1* | 9/2017 | Moore | A23K 50/10 |
| 2018/0282481 | A1* | 10/2018 | Beckham | B01D 3/106 |
| 2018/0297726 | A1* | 10/2018 | Ruben | B65B 63/005 |
| 2018/0304274 | A1* | 10/2018 | Bates | A61K 36/00 |
| 2018/0325973 | A1* | 11/2018 | Nowak | A61K 9/0014 |
| 2018/0333446 | A1* | 11/2018 | Shan | A61K 36/185 |
| 2019/0192422 | A1* | 6/2019 | Shibaz | A61K 9/007 |

OTHER PUBLICATIONS

A systematic review of the antipsychotic properties of cannabidiol in humans (Year: 2015).*

Clinicians' Guide to Cannabidiol and Hemp Oils (Year: 2019).*

Roth WIPO Patentscope Translated Specification and Claims (Year: 2021).*

BE 584191 WIPO Patentscope Translation (Year: 2021).*

* cited by examiner

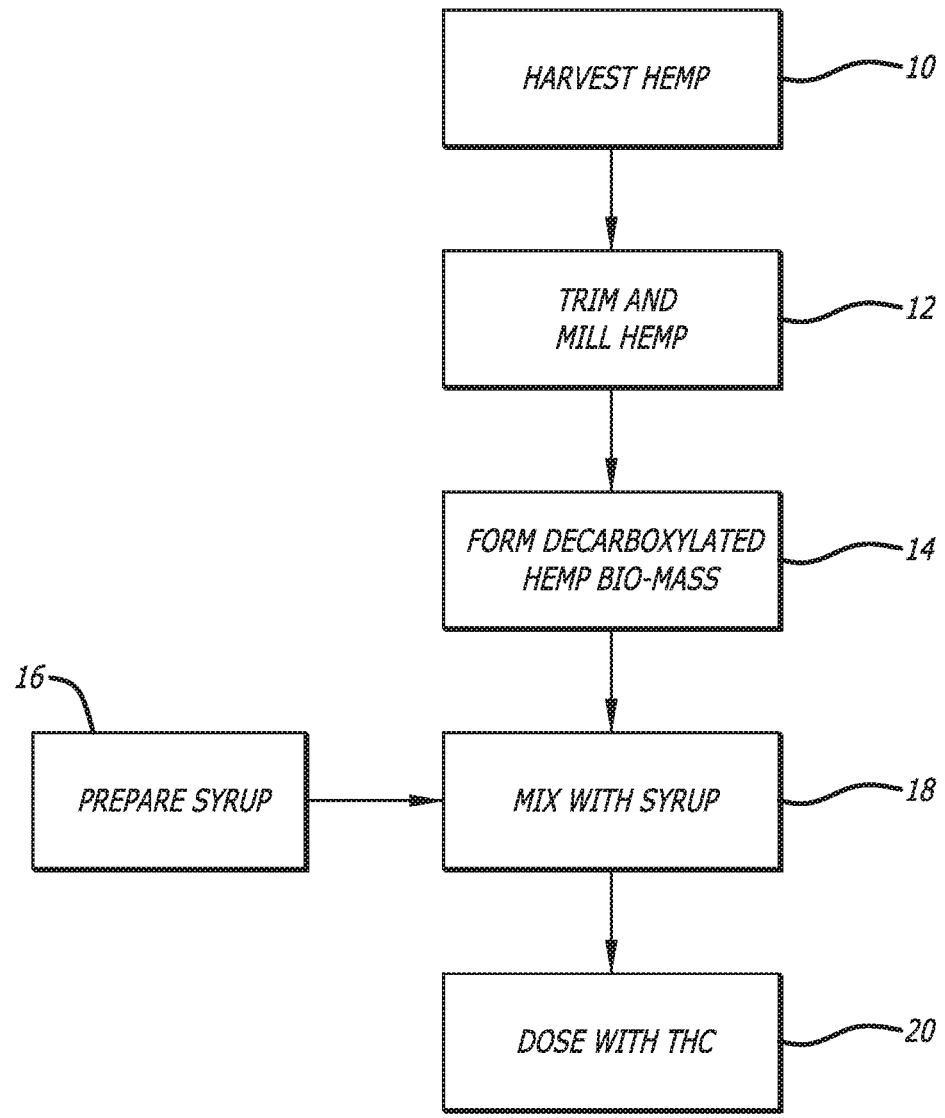

HEMP LEAF CHEW COMPOSITION AND METHOD FOR PRODUCING

BACKGROUND

Various forms of tobacco are known, including cigarettes, cigars, and chewing tobacco. There are known health risks with all types of tobacco products.

The popularity of cannabis is increasing and there are now known medical benefits of cannabidiol (CBD and CBDA), including antibacterial and anti-nausea properties. Furthermore, CBDA may help to control growth of tumors in cancer patients.

What is needed is a substitute for a chewing tobacco. Also, what is needed is a form of medical marijuana in a smokeless chew. Furthermore, what is needed is a form of medical marijuana that does not require smoking, but may be ingested orally or sub-lingually through the gums.

SUMMARY

Briefly, and in general terms, the present disclosure is directed to a method for preparing a hemp leaf chew. The method may include decarboxylating hemp and then mixing decarboxylated hemp with a syrup to create the hemp leaf chew. The hemp leaf chew is meant to be chewed by a user similar to chewing tobacco. In other embodiments, the method may include curing hemp and milling the cured hemp. Once harvested, the hemp may be formed into a biomass that includes 25% leaf material, 25% stalk and stem, and 50% flower and flower trim. These percentages are only approximations and may vary by up to 20%. In this method, decarboxylating hemp includes heating the milled hemp until it is sufficiently dried as desired. In one embodiment, the milled hemp will be heated until it turns brown in color. In one embodiment, the milled hemp may be heated at approximately 200 degrees Fahrenheit for approximately 60 minutes, although temperature and heating time may vary.

In one embodiment, the method may include preparing a syrup that can be mixed with the milled hemp to create the hemp leaf chew. In certain embodiments, the syrup may include a fruit juice, such as apple, cherry, or cranberry. However, any fruit juice may be used. In other embodiments, the syrup may include pepper, salt, hemp oil, olive oil, chipotle powder, coconut oil, or pumpkin seed oil or sunflower seed oil. Other ingredients may also be used to change the flavor of the hemp leaf chew and to preserve the hemp leaf chew.

In another embodiment, the method may further include dosing the hemp leaf chew with THC. Any amount of THC may be used as desired, but in one embodiment, up to 15 mg of THC per serving and about 100 mg per package of THC is used to dose the hemp leaf chew. In certain other embodiments, the hemp leaf chew will only include CBD (from the decarboxylation). Once prepared, the hemp leaf chew may be packaged in a container, and the container may have an air tight seal to preserve the hemp leaf chew. The hemp leaf chew may also be formed into pellets. In other embodiments, the hemp leaf chew in a snus package. Depending on the embodiment, the pellets or snus packages of the hemp leaf chew may be dosed with up to 15 mg THC and placed in the user's top or bottom lip for sub-lingual absorption and consumption by user. The use may be as a replacement for chewing tobacco. Also, the use may be recreational if the hemp leaf chew is dosed with THC. In other embodiments, the hemp leaf chew containing CBD with little or no THC, such as up to 0.3% THC on a dry weight basis may be used for medicinal purposes.

The disclosure may also include about 25 g hemp leaf chew product that includes 10 g milled hemp that may contain up to 175.8 mg (or about 0.52%) of CBD, and the hemp leaf chew product may contain up to 15 g (about 55%) of an organic syrup. In another embodiment, the hemp leaf chew may include up to 15 mg of THC, but maybe only 10 mg of THC. Each portion of the hemp leaf chew, such as a single container, may contain up to 26 g of treated hemp bio-mass, 15 g of which will typically be syrup and 10 g hemp bio-mass. These amounts may be scaled up or down depending on the desired amount of hemp leaf chew product.

Other features and advantages will become apparent from the following detailed description, taken in conjunction with the accompanying drawings, which illustrate by way of example, the features of the various embodiments.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1 depicts a flow diagram of an exemplary method for forming a hemp leaf chew composition.

DETAILED DESCRIPTION

The present disclosure is directed generally to a method of preparing a hemp based chew or smokeless hemp based composition.

Each of the features and teachings disclosed herein can be utilized separately or in conjunction with other features and teachings to provide a hemp leaf chew. Furthermore, the current disclosure can be used to provide a variety of hemp leaf chew including THC, THC-A, CBD, or CBD-A. The embodiments of the hemp leaf chew can be used for recreational purposes and medical purposes. Also, the hemp leaf chew is a substitute for chewing tobacco. This detailed description is merely intended to teach a person of skill in the art further details for practicing the present teachings and is not intended to limit the scope of the claims. Therefore, combinations of features disclosed in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that these specific details are not required to practice the teachings of the present disclosure.

With reference to FIG. 1, a flow diagram shows the steps for one embodiment of making a hemp leaf chew. At step 10, hemp is harvested. In one embodiment, the hemp is a sativa strain cannabis containing less than about 0.3% THC-A and over about 4% CBD-A on a dry weight basis. Using hemp biomass, a manufacturer may create a blend including about 25% leaf material, 25% stalk and stem and 50% flower and flower trim. These percentages are approximations and may vary by up to 20%. Next, once the hemp is harvested, it is trimmed and milled at step 12. In one embodiment, the hemp will be milled to size to provide the right texture for flavoring and packaging. In one embodiment, the use of a Hammer Mill will bring the biomass to approximately 1/64" to approximately 1/16". The approximate measurements given may vary by up to 20%. The fine powder may be used in snus packs and the larger particulate may provide texture for loose chew products.

In step 14, the hemp undergoes decarboxylation. As is known in the art, decarboxylation means a chemical reaction is created that removes a carboxyl group and releases carbon dioxide gas. This process converts inactive components in cannabis, which are not psychoactive, into active components. The two main catalysts in the decarboxylation process are heat and time. Curing and drying cannabis over time will result in partial decarboxylation. Smoking and vaporizing can instantly decarboxylate cannabinoids as a result of the extremely high temperatures that are present, and this makes them immediately available for absorption via inhalation. However, people with respiratory conditions, children, or the elderly who are attempting to use cannabis for its medicinal purposes likely will not want to inhale the smoke, so extracting numerous cannabinoids and terpenes in the form of oil is often preferred. In this form, a user may absorb the cannabinoids and terpenes sub-lingually.

In one embodiment, the decarboxylation process may include heating the cannabis leaf, trim and flowers (biomass) to about 200 degrees Fahrenheit for about 60 minutes. The cannabis may need to be mixed or stirred to ensure even toasting. After the cannabis has turned a medium brown color and is dried as desired, the cannabis is removed from the heat and allowed to cool. It should be understood that the cannabis may be heated at any temperatures from about 200 degrees Fahrenheit to about 300 degrees Fahrenheit for about 30 minutes to about 60 minutes as needed to ensure the cannabis is sufficiently dried. These temperatures and time are approximations and may vary by 20%.

In step 16, syrup is prepared. The syrup helps bind the hemp leaf chew together and also adds flavor. Any flavor may be used such as mint, cherry, or even no flavor. In one embodiment, the syrup may include a juice, such as apple, cherry and cranberry. Further ingredients of the syrup may include cayenne pepper, chipotle powder, salt, hemp oil, olive oil, coconut oil, pumpkin seed oil, sunflower seed oil, mint oil, peppermint oil, natural and artificial flavors, sodium citrate, sodium carbonate, ammonium chloride, ammonium carbonite, ethyl alcohol, preservatives, molasses, coffee, vegetable glycerin, mint extract, liquid smoke flavoring, mint water, or tart cherry extract. Some or all of these ingredients may be used to form the syrup. In one embodiment, a base stock that is used to form the syrup includes: a fruit juice, such as apple, cranberry, cherry, grape, peach, or any other fruit, sodium carbonate, sodium citrate, cayenne pepper, chipotle pepper, coffee, peppermint extract (alcohol), liquid smoke mesquite flavoring, mint oil, hemp oil, liquid smoke oil, coconut oil, olive oil, pumpkin seed oil, vegetable glycerin, and molasses. In a preferred embodiment, the syrup may be formed using the following ingredients: up to 500 g fruit juice, 6 g salt, 3 g cayenne pepper, 3 g chipotle powder, 2 g coffee (espresso ground or similar), 3 g hemp oil, 3 g peppermint oil, 15 g vegetable glycerin, 20 g molasses, 2 tsp Mint water, 1/8 tsp Hickory Liquid Smoke flavoring, 2.5 tsp Mint Extract (Ethyl Alcohol), and 2.5 tsp Tart cherry extract. These measurements are approximations and may vary by up to 20%.

Once the ingredients are mixed with proper proportions per unit that will create the base stock, the base stock is brought to a boil to create the syrup. In one embodiment the base stock of the syrup is boiled for approximately 10 minutes. After approximately 10 minutes of boiling, the base stock turns into a syrup. Various heats and times may be applied in order to boil the stock. The syrup is removed from the heat source and allowed to cool to about 180 degrees Fahrenheit.

Next, at step 18, the milled decorboxylated hemp biomass is mixed into the syrup. In the preferred embodiment, approximately 45 g decarboxylated hemp bio-mass is mixed with the syrup to produce approximately 130-150 g (depending on evaporation of water from syrup) of the hemp leaf chew. In one embodiment, the produced about 5.5 finished cans, 45 pellets, or up to 130 snus packets. The ingredients for the preferred embodiment may be scaled up or down depending on the amount of product desired. Once the hemp blend is mixed with flavored syrup it may be placed in an airtight container either storage or packaging.

In one embodiment, an additional step 20 may be performed to the hemp blend to dose it with Tetrahydrocannabinol (THC). Dosing decarboxylated flavored hemp chew with up to 15 mg THC may be performed. In some embodiments the hemp chew is dosed with a tincture/extract that includes THC. In one embodiment, 0.33 ml of a tincture/extract may contain up to about 10 mg of activated THC from a variety of strains, in doing this the manufacturer is turning a non-psychoactive cannabis that naturally has less than 0.3% THC on a dry weight basis into a controlled delivery system for THC. While providing access to the full spectrum of cannabinoids provided by hemp most notably CBD. The dosing of hemp is turning hemp into marijuana that can be regulated and standardized for consistent consumption and results.

Once the hemp chew, with or without additional dosing of THC is formed, it may be packaged. In one embodiment the chew may be packaged loose in a can, approximately 25 g, for the non-dosed hemp leaf chew or for the THC dosed hemp leaf chew. In certain embodiments, the flavored hemp biomass will be pressed into forms that can be portion controlled for weight and dosage. In one embodiment, the pellets (form) of the hemp leaf chew may be in pellet form that are approximately 1 g to approximately 3.125 g in size.

In other embodiments, the hemp leaf chew may be packaged with dosed and non-dosed hemp in snus packs. Various sizes, such as 0.5 g, 1.5 g, or any size may be used for the packaging.

Variations may be made to the embodiments described herein without departing from the scope of the present disclosure. All the elements described and claimed may be replaced by equivalent elements and the parts, materials, shapes and dimensions may be chosen as needed.

What is claimed:

1. A method for preparing a hemp leaf chew, the method comprising:
   milling hemp, wherein the hemp is formed into a biomass of 10-25% leaf material, 10-25% stalk and stem, and 50-85% flower and flower trim, to a size between approximately 1/64 inch and approximately 1/16 inch, wherein the hemp comprises leaf, trim and flowers;
   heating the hemp in order to decarboxylate the hemp to create a decarboxylated hemp;
   without extracting CBD from the decarboxylated hemp, mixing the decarboxylated hemp with a syrup to create the hemp leaf chew;

wherein decarboxylating the hemp includes heating the hemp at a temperature between 180 degrees and 300 degrees Fahrenheit for between 30 and 60 minutes.

2. The method of claim 1, further comprising stirring the hemp to ensure even curing.

3. The method of claim 1, further comprising preparing the syrup.

4. The method of claim 3, wherein the syrup includes a fruit juice, pepper, salt, hemp oil, olive oil, chipotle powder, coconut oil, or pumpkin seed oil.

5. The method of claim 1, further comprising dosing the hemp leaf chew with Tetrahydrocannabinol.

6. The method of claim 1, further comprising packaging the hemp leaf chew in a container.

7. The method of claim 1, further comprising packaging the hemp leaf chew in a snus package.

8. The method of claim 1, wherein the hemp is formed into a biomass of 25% leaf material, 25% stalk and stem, and 50% flower and flower trim.

9. The method of claim 1, wherein the hemp is formed into a biomass of 15% leaf material, 15% stalk and stem, and 70% flower and flower trim.

\* \* \* \* \*